United States Patent
Cassin

(10) Patent No.: US 9,622,946 B2
(45) Date of Patent: Apr. 18, 2017

(54) EMULSION CONTAINING ORGANOSILICON-BASED PORTIONS OF HOLLOW SPHERES

(71) Applicant: L'OREAL, Paris (FR)

(72) Inventor: Guillaume Cassin, Villebon sur Yvetter (FR)

(73) Assignee: L'OREAL, Paris (FR)

( * ) Notice: Subject to any disclaimer, the term of this patent is extended or adjusted under 35 U.S.C. 154(b) by 0 days.

(21) Appl. No.: 13/770,747

(22) Filed: Feb. 19, 2013

(65) Prior Publication Data

US 2013/0224267 A1    Aug. 29, 2013

Related U.S. Application Data

(63) Continuation of application No. 13/110,486, filed on May 18, 2011, now abandoned, which is a continuation of application No. 10/982,925, filed on Nov. 8, 2004, now abandoned.

(60) Provisional application No. 60/529,754, filed on Dec. 17, 2003.

(30) Foreign Application Priority Data

Nov. 13, 2003   (FR) ..................... 03 50829

(51) Int. Cl.
| | |
|---|---|
| *A01N 59/02* | (2006.01) |
| *A61K 33/04* | (2006.01) |
| *A61K 8/02* | (2006.01) |
| *A61K 8/06* | (2006.01) |
| *A61K 8/11* | (2006.01) |
| *A61Q 1/00* | (2006.01) |
| *A61Q 19/00* | (2006.01) |
| *A61Q 19/08* | (2006.01) |
| *A61Q 19/02* | (2006.01) |

(52) U.S. Cl.
CPC ............... *A61K 8/025* (2013.01); *A61K 8/06* (2013.01); *A61K 8/11* (2013.01); *A61Q 1/00* (2013.01); *A61Q 19/00* (2013.01); *A61Q 19/007* (2013.01); *A61Q 19/008* (2013.01); *A61Q 19/02* (2013.01); *A61Q 19/08* (2013.01); *A61K 2800/412* (2013.01)

(58) Field of Classification Search
None
See application file for complete search history.

(56) References Cited

U.S. PATENT DOCUMENTS

| | | | |
|---|---|---|---|
| 5,593,680 A * | 1/1997 | Bara et al. ................... | 424/401 |
| 5,814,311 A * | 9/1998 | Le Bras-Roulier et al. ... | 424/69 |
| 2003/0228339 A1* | 12/2003 | El-Nokaly et al. .......... | 424/401 |

FOREIGN PATENT DOCUMENTS

| | | |
|---|---|---|
| EP | 0 254 612 | 1/1988 |
| FR | 2224126 | * 12/1974 |
| FR | 2 816 500 | 5/2002 |
| JP | 2001-31524 | 2/2001 |
| JP | 200131524 | * 2/2001 |
| JP | 2001-278746 | 10/2001 |
| JP | 2001278746 | * 10/2001 |
| JP | 2003-128788 | 5/2003 |
| JP | 2003128788 | * 5/2003 |
| WO | WO 03/020225 | 3/2003 |

OTHER PUBLICATIONS

Office Action mailed Mar. 14, 2006, in Japanese Patent Application No. 2004-329708, filed Nov. 12, 2004.
Office Action mailed Dec. 19, 2006, in Japanese Patent Application No. 2004-329708, filed Nov. 12, 2004.

* cited by examiner

*Primary Examiner* — Alton Pryor
(74) *Attorney, Agent, or Firm* — Oblon, McClelland, Maier & Neustadt, L.L.P.

(57) ABSTRACT

The present invention relates to a composition in the form of an emulsion containing portions of hollow spheres of organosilicon-based material, the portions of hollow spheres having a mean diameter ranging from 0.05 to 10 μm. The invention also relates to physiologically acceptable emulsion compositions comprising hollow spheres, and to a process for fading out skin surface defects, in particular to reduce the sheen of the skin and/or to fade out pores, shadows under the eyes, marks, wrinkles and/or fine lines, comprising the topical application to the skin of the above-mentioned compositions.

35 Claims, 1 Drawing Sheet

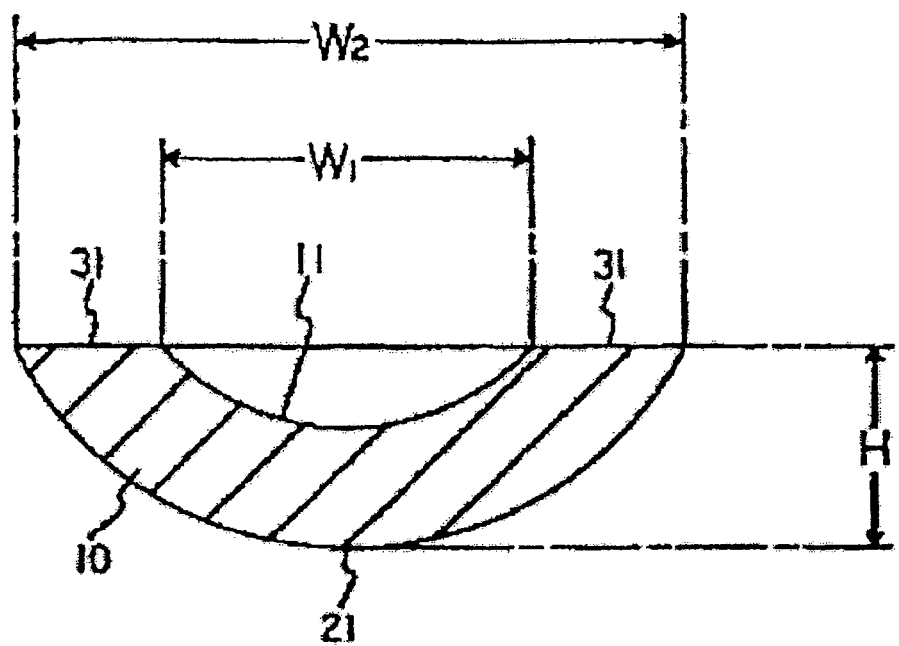

EMULSION CONTAINING ORGANOSILICON-BASED PORTIONS OF HOLLOW SPHERES

REFERENCE TO PRIOR APPLICATIONS

This application is a continuation application of U.S. application Ser. No. 10/982,925, filed Nov. 8, 2004, and claims priority to U.S. provisional application 60/529,754 filed Dec. 17, 2003, and to French patent application 0350829 filed Nov. 13, 2003, both incorporated herein by reference.

FIELD OF THE INVENTION

The present invention relates to a composition in the form of an emulsion comprising portions of hollow spheres, sometimes termed hollow sphere portions herein, of an organosilicon-based material, the spheres having a mean diameter ranging from 0.05 to 10 µm.

The invention also relates to physiologically acceptable emulsion compositions comprising portions of hollow spheres, and to a process for fading out skin surface defects, in particular to reduce the sheen of the skin and/or to fade out pores, shadows under the eyes, marks, wrinkles and/or fine lines, comprising the topical application to the skin of the above-mentioned compositions.

Additional advantages and other features of the present invention will be set forth in part in the description that follows and in part will become apparent to those having ordinary skill in the art upon examination of the following or may be learned from the practice of the present invention. The advantages of the present invention may be realized and obtained as particularly pointed out in the appended claims. As will be realized, the present invention is capable of other and different embodiments, and its several details are capable of modifications in various obvious respects, all without departing from the present invention. The description is to be regarded as illustrative in nature, and not as restrictive.

BACKGROUND OF THE INVENTION

When the light hits the surface of the skin, it separates into two components: a transmitted component and a reflected component. The transmitted light is itself divided into a component of specular or direct transmission (at a single angle) and a component of diffuse transmission (in all directions). The reflected light is also divided into a component of diffuse reflection (in all directions) and a component of specular reflection (at a single angle).

It is known that, depending on their size, shape and chemical nature, pulverulent materials interfere with the various components of light above and as a result have the capacity to modify the appearance of the skin.

Research has become focused in recent years on powders with high diffuse reflectance, low specular reflectance and high diffuse transmittance, which make it possible especially to reduce the appearance of wrinkles and fine lines by reducing the difference in luminosity between the valley and the edges of wrinkles.

These powders, known as "soft-focus" powders, also make it possible to give shiny skins a more matt appearance.

Now, obtaining a matt effect on the skin is highly sought by users with combination or greasy skin, and also for cosmetic compositions intended to be used in hot and humid climates. The reason for this is that the highlights caused by an excess of sebum on the surface of the skin are generally considered as unattractive.

Among the soft-focus powders proposed in the prior art, mention may be made of certain micas coated with minerals and/or with PMMA, optionally coated silica microspheres, nylon powders, boron nitride, or talc with a granulometry (or mean particle size) of 1.8 microns.

It nevertheless remains that there is still a need for materials that allow the surface defects of the skin to be camouflaged.

SUMMARY OF THE INVENTION

The inventor has now discovered, surprisingly and unexpectedly, that portions of certain silicone particles, including those obtained by condensation of silanols resulting from the hydrolysis of organosilicon-based compounds, make it possible to satisfy this need when they are formulated as an emulsion.

DETAILED DESCRIPTION OF THE PREFERRED EMBODIMENTS

One subject of the present invention is thus a composition in the form of an emulsion comprising, preferably in a physiologically acceptable medium, portions of hollow spheres comprising, consisting essentially of, or consisting of, organosilicon-based material, the spheres having a mean diameter ranging from 0.05 to 10 µm. In preferred embodiments the portions of hollow spheres consist of organosilicon-based material.

The invention also relates to a process for fading out surface defects of the skin, especially of greasy or combination skin or aged skin, in particular to reduce the sheen of the skin and/or to fade out pores, shadows under the eyes, marks, wrinkles and/or fine lines, comprising the topical application to the skin of the above-mentioned composition.

The emulsions of the invention are preferably products with a non-greasy feel in which the optical properties are exploited to camouflage skin imperfections, wherein optional skincare active agents might possibly act simultaneously on the causes of these imperfections.

Invention particles, which have the form of hollow spheres, have already been described in patent applications JP-2003 128 788 and JP-2000 191 789. In these patent applications, it is suggested to use them especially in cosmetic products for the face or in makeup products, in particular in foundation compact powders. For an application in the makeup field, these particles may be formulated in the presence of water and surfactants. However, it is not suggested to use them in emulsions.

For the purposes of the present invention, the term "emulsion" means a system comprising at least two phases of two or more immiscible or partially miscible liquids, one of which—which forms the dispersed phase—is dispersed in the other—which forms the continuous phase—in the form of fine droplets whose diameter generally does not exceed 5 microns.

For the purposes of the present invention, the terms "portions of hollow spheres," and "hollow sphere portions," mean the same thing and refer to a portion, or part, of a hollow sphere. Such portions or parts may have any shape, such as the shape of a cup, bowl, vase, etc., and are preferably substantially hemispherical, understanding that the spheres can be cut across at any height, thus providing, e.g., portions in the form of truncated hollow spheres, with a single orifice communicating with their central cavity, and having a transverse cross section in the form of a horseshoe or a bow. Preferably, the portions of hollow spheres consist of organosilicon material.

The silicon material constituting these hollow sphere portions, in whole or in part, is preferably a crosslinked polysiloxane of three-dimensional structure; it preferably comprises, or even consists of, units of formula (I): $SiO_2$ and of formula (II): $R^1SiO_{1.5}$ in which $R^1$ denotes an organic group containing a carbon atom directly linked to the silicon atom. The organic group may be a reactive organic group or an unreactive organic group, and preferably an unreactive organic group.

The unreactive organic group may be a $C_1$-$C_4$ alkyl group, especially a methyl, ethyl, propyl or butyl group, or a phenyl group, and preferably a methyl group.

The reactive organic group may be an epoxy group, a (meth)acryloxy group, an alkenyl group, a mercaptoalkyl, aminoalkyl or haloalkyl group, a glyceroxy group, a ureido group or a cyano group. Preferably, the reactive organic group may be an epoxy group, a (meth)acryloxy group, an alkenyl group or a mercaptoalkyl or aminoalkyl group. The reactive organic group generally contains from 2 to 6 carbon atoms and especially from 2 to 4 carbon atoms.

Epoxy groups that may be mentioned include a 2-glycidoxyethyl group, a 3-glycidoxypropyl group or a 2-(3,4-epoxycyclohexyl)propyl group.

(Meth)acryloxy groups that may be mentioned include a 3-methacryloxypropyl group or a 3-acryloxypropyl group.

Alkenyl groups that may be mentioned include a vinyl, allyl or isopropenyl group.

Mercaptoalkyl groups that may be mentioned include a mercaptopropyl or mercaptoethyl group.

Aminoalkyl groups that may be mentioned include a 3-(2-aminoethyl)aminopropyl group, a 3-aminopropyl group or an N,N-dimethylaminopropyl group.

Haloalkyl groups that may be mentioned include a 3-chloropropyl group or a trifluoropropyl group.

Glyceroxy groups that may be mentioned include a 3-glyceroxypropyl group or a 2-glyceroxyethyl group.

A ureido group that may be mentioned is a 2-ureidoethyl group.

Cyano groups that may be mentioned include a cyanopropyl or cyanoethyl group.

Preferably, $R_1$ denotes a methyl group.

Portinos of hollow spheres that are useful herein include those that may be obtained according to a process that comprises:
(a) introducing into an aqueous medium, in the presence of at least one hydrolysis catalyst, and optionally of at least one surfactant, a compound (I) of formula $SiX_4$ and a compound (II) of formula $RSiY_3$, in which X and Y independently denote a $C_1$-$C_4$ alkoxy group, an alkoxyethoxy group containing a $C_1$-$C_4$ alkoxy group, a $C_2$-$C_4$ acyloxy group, an N,N-dialkylamino group containing a $C_1$-$C_4$ alkyl group, a hydroxyl group, a halogen atom or a hydrogen atom, and R denotes an organic group comprising a carbon atom directly linked to the silicon atom and especially has the meaning given above for $R_1$; and
(b) placing the mixture resulting from step (a) in contact with an aqueous solution containing at least one polymerization catalyst and optionally at least one surfactant, at a temperature of between 30 and 85° C., for at least two hours.

Step (a) can be termed a hydrolysis reaction and step (b) a condensation reaction.

As regards the groups X and Y of compounds (I) and (II), the following may be used:

as $C_1$-$C_4$ alkoxy groups: methoxy or ethoxy groups;
as alkoxyethoxy groups containing a $C_1$-$C_4$ alkoxy group: methoxyethoxy or butoxyethoxy groups;
as $C_2$-$C_4$ alkyloxy groups: acetoxy or propoxy groups;
as N,N-dialkylamino groups containing a $C_1$-$C_4$ alkyl group: dimethylamino or diethylamino groups;
as halogen atoms: chlorine or bromine atoms.

Preferably, X and/or Y denotes a $C_1$-$C_4$ alkoxy group.

Thus, preferred compounds of formula (I) that may be mentioned include: tetramethoxysilane, tetraethoxysilane, tetrabutoxysilane, trimethoxyethoxysilane, tributoxyethoxysilane, tetraacetoxysilane, tetra-propoxysilane, tetraacetoxysilane, tetra(dimethylamino)silane, tetra(diethylamino)silane, silane tetraol, chlorosilane triol, dichlorodisilanol, tetrachlorosilane, chlorotrihydrogenosilane. Preferably, the compound of formula (I) is selected from the group consisting of tetramethoxysilane, tetraethoxysilane and tetrabutoxysilane, and mixtures thereof.

Preferred compounds of formula (II) comprising an unreactive organic group R that may be mentioned include: methyltrimethoxysilane, ethyltriethoxysilane, propyltributoxysilane, butyltributoxysilane, phenyltrimethoxyethoxysilane, methyltributoxyethoxysilane, methyltriacetoxysilane, methyltripropoxysilane, methyltriacetoxysilane, methyltri(dimethylamino)silane, methyltri(diethylamino)silane, methylsilane triol, methylchlorodisilanol, methyltrichlorosilane and methyltrihydrogenosilane.

Finally, preferred compounds of formula (II) comprising a reactive organic group R that may be mentioned include:
silanes containing an epoxy group, for instance 3-glycidoxypropyl trimethoxysilane, 3-glycidoxypropyl triethoxysilane, 2-(3,4-epoxycyclohexyl)ethyl trimethoxysilane, 3-glycidoxypropylmethyl dimethoxysilane, 3-glycidoxypropylmethyl dimethoxysilane, 2-glycidoxyethylmethyl dimethoxysilane, 3-glycidoxypropyl dimethylmethoxysilane and 2-glycidoxyethyl dimethylmethoxysilane;
silanes containing a (meth)acryloxy group, for instance 3-methacryloxypropyl trimethoxysilane and 3-acryloxypropyl trimethoxysilane;
silanes containing an alkenyl group, for instance vinyl trimethoxysilane, allyl trimethoxysilane and isopropenyl trimethoxysilane;
silanes containing a mercapto group, for instance mercaptopropyl trimethoxysilane and mercaptoethyl trimethoxysilane;
silanes containing an aminoalkyl group, for instance 3-aminopropyl trimethoxysilane, 3-(2-aminoethyl)aminopropyl trimethoxysilane, N,N-dimethylaminopropyl trimethoxysilane and N,N-dimethylaminoethyl trimethoxysilane;
silanes containing a haloalkyl group, for instance 3-chloropropyl trimethoxysilane and trifluoropropyl trimethoxysilane;
silanes containing a glyceroxy group, for instance 3-glyceroxypropyl trimethoxysilane and bis(3-glyceroxypropyl) dimethoxysilane;
silanes containing a ureido group, for instance 3-ureidopropyl trimethoxysilane, 3-ureidopropyl methyldimethoxysilane and 3-ureidopropyl dimethylmethoxysilane;
silanes containing a cyano group, for instance cyanopropyl trimethoxysilane, cyanopropyl methyldimethoxysilane and cyanopropyl dimethylmethoxysilane.

Highly preferred examples of compounds of this type of formula (II) are selected from the group consisting of: silanes containing an epoxy group, silanes containing a (meth)acryloxy group, silanes containing an alkenyl group, silanes containing a mercapto group and silanes containing an aminoalkyl group.

Examples of compounds (I) and (II) that are highly preferred for performing this invention are, respectively, tetraethoxysilane and methyltrimethoxysilane. After polymerization of these units, the sphere portions according to the invention thus advantageously have a crosslinked structure consisting of $SiO_2$ units and of $R_1SiO_{1.5}$ units in which $R_1$ is preferably a methyl group.

In step (a), the molar ratio of compound (I) to compound (II) usually ranges from 30:70 to 50:50, advantageously from 35:65 to 45:55 and is preferably 40:60. The weight ratio of water to the total amount of compounds (I) and (II) preferably ranges from 10:90 to 70:30. The order of introduction of compounds (I) and (II) generally depends on their rate of hydrolysis. The temperature of the hydrolysis reaction usually ranges from 0° C. to 40° C. and usually does not exceed 30° C. so as to avoid premature condensation of the compounds.

Hydrolysis and polymerization catalysts that may be used include basic catalysts—such as sodium hydroxide, sodium carbonate or amines- or acidic catalysts, selected from the group consisting of organic acids—such as acetic acid or sodium dodecylbenzenesulfonate- or mineral catalysts—such as hydrochloric acid. When it is present, the surfactant is preferably a nonionic or anionic surfactant or a mixture of the two. Sodium dodecylbenzenesulfonate may be used as anionic surfactant. The end of hydrolysis is marked by the disappearance of the water-insoluble products (I) and (II), and the production of a homogeneous liquid layer.

The condensation step (b) can use the same catalyst as the hydrolysis step and/or another catalyst selected from the group consisting of those mentioned above.

After this process, a suspension in water of fine organosilicon-based particles is obtained, which may then optionally be separated from their medium. The process described above can thus include an additional filtration step, for example through a membrane filter, of the product resulting from step (b), optionally followed by a step of centrifugation of the filtrate, which is intended to separate the particles from the liquid medium, and then a step of drying the particles. Needless to say, other separation methods may be used.

The spheres obtained have a mean diameter ranging from 0.05 to 10 μm.

The form and dimensions of the hollow sphere portions obtained according to the above process will depend especially on the mode of bringing the products into contact in step (b).

A rather basic pH and cold introduction of the polymerization catalyst into the mixture obtained in step (a) will lead to hollow sphere portions in the form of round-bottomed "bowls", whereas a rather acidic pH and dropwise introduction of the mixture obtained in step (a) into the hot polymerization catalyst will lead to hollow sphere portions having a transverse cross section in the form of a "horseshoe".

According to one preferred embodiment of the invention, hollow sphere portions in the form of "bowls" are used. These may be obtained as described in patent application JP-2003 128 788.

The attached FIGURE illustrates sphere portions of this type in transverse cross section.

As is seen from this FIGURE, these sphere portions are formed (in longitudinal cross section) from a small inner arc (11), a large outer arc (21) and segments (31) linking the ends of the respective arcs, the width (W1) between the two ends of the small inner arc (11) ranging from 0.01 to 8 μm and preferably from 0.02 to 6 μm on average, the width (W2) between the two ends of the large outer arc (21) ranging from 0.05 to 10 μm on average and the height (H) of the large outer arc (21) ranging from 0.015 to 8 μm on average. The segments (31) preferably have a length (W2−W1)/2 (referred to hereinbelow as the "particle thickness") ranging from 0.05 to 1 μm and more preferably from 0.1 to 0.8 μm.

The dimensions mentioned above are obtained by calculating the average dimensions of one hundred particles selected from the group consisting of an image obtained using a scanning electron microscope.

According to one advantageous embodiment of the invention, the ratio Ra of the width W2 to the thickness (W2−W1)/2 is at least equal to 3, preferably greater than 5 and better still greater than 10, or even greater than 20. Specifically, the inventor has discovered that the higher this ratio, the better the optical properties of the materials according to the invention and the smaller the amount of material required to obtain a desired effect.

As sphere portions that may be used according to the invention, mention may be made of the bowl-shaped particles sold in the series NLK by the company Takemoto Oil & Fat, which consist of crosslinked organosilicone TAK-110 (methylsilanol/silicate crosslinked polymer) from this same company, in particular the particles sold under the name NLK-506.

The amount of sphere portions used in the composition according to the invention is not limited and can represent, for example, from 0.1% to 20%, preferably from 0.5% to 15% and better still from 0.5% to 10% of the total weight of the composition.

The composition according to the invention is preferably suitable for topical application to the skin and thus generally comprises a physiologically acceptable medium, i.e. a medium that is compatible with the skin and possibly with its integuments. Preferably, it is a cosmetically acceptable medium, i.e. a medium that has a pleasant appearance, in particular colour, odour and feel, and that does not cause discomfort (redness, stinging or tautness) liable to put the user off the composition.

The composition according to the invention may be in the form of an emulsion obtained by dispersing an aqueous phase in a fatty phase (W/O) or a fatty phase in an aqueous phase (O/W), of liquid or semi-liquid consistency of the milk type, or of soft, semi-solid or solid consistency of the cream or gel type, or alternatively a multiple emulsion (W/O/W or O/W/O). These compositions can prepared according to the usual methods known to those of ordinary skill in this art in view of this disclosure.

The composition according to the invention may be in the form of a care or makeup product for the face and/or the body, and may be packaged, for example, in the form of cream in a jar or fluid in a tube or in a pump-dispenser bottle.

According to one preferred embodiment of the invention, the composition is in the form of an O/W emulsion.

As non-limiting examples of oils that may be used in the composition of the invention, mention may be made of:
  hydrocarbon-based oils of animal origin, such as perhydrosqualene;
  hydrocarbon-based oils of plant origin, such as liquid triglycerides of fatty acids containing from 4 to 10 carbon atoms, for instance heptanoic or octanoic acid triglycerides or alternatively, for example, sunflower oil, maize oil, soybean oil, marrow oil, grapeseed oil, sesame seed oil, hazelnut oil, apricot oil, macadamia oil, arara oil, sunflower oil, castor oil, avocado oil, caprylic/capric acid triglycerides, for instance those sold by the company Stearineries Dubois or those sold under the names Miglyol 810, 812 and 818 by the company Dynamit Nobel, jojoba oil or shea butter oil;

synthetic esters and synthetic ethers, especially of fatty acids, for instance oils of formulae $R^1COOR^2$ and $R^1OR^2$ in which $R^1$ represents the fatty acid residue containing from 8 to 29 carbon atoms and $R^2$ represents a branched or unbranched hydrocarbon-based chain containing from 3 to 30 carbon atoms, such as, for example, purcellin oil, isononyl isononanoate, isopropyl myristate, 2-ethylhexyl palmitate, 2-octyldodecyl stearate, 2-octyldodecyl erucate or isostearyl isostearate; hydroxylated esters such as isostearyl lactate, octyl hydroxystearate, octyldodecyl hydroxystearate, diisostearyl malate, triisocetyl citrate and fatty alkyl heptanoates, octanoates and decanoates; polyol esters, for instance propylene glycol dioctanoate, neopentyl glycol diheptanoate and diethylene glycol diisononanoate; and pentaerythritol esters, for instance pentaerythrityl tetraisostearate;

linear or branched hydrocarbons of mineral or synthetic origin, such as volatile or non-volatile paraffin oils, and derivatives thereof, isohexadecane, isododecane, petroleum jelly, polydecenes, and hydrogenated polyisobutene such as Parleam® oil;

natural or synthetic essential oils such as, for example, eucalyptus oil, lavandin oil, lavender oil, vetiver oil, Litsea cubeba oil, lemon oil, sandalwood oil, rosemary oil, camomile oil, savory oil, nutmeg oil, cinnamon oil, hyssop oil, caraway oil, orange oil, geraniol oil, cade oil and bergamot oil;

fatty alcohols containing from 8 to 26 carbon atoms, for instance cetyl alcohol, stearyl alcohol and the mixture thereof (cetylstearyl alcohol), octyldodecanol, 2-butyloctanol, 2-hexyldecanol, 2-undecylpentadecanol, oleyl alcohol or linoleyl alcohol;

partially hydrocarbon-based and/or partially silicone-based fluoro oils, for instance those described in document JP-A-2 295 912;

silicone oils, for instance volatile or non-volatile polymethylsiloxanes (PDMSs) containing a linear or cyclic silicone chain, that are liquid or pasty at room temperature, especially cyclopolydimethylsiloxanes (cyclomethicones) such as cyclohexasiloxane and cyclopentasiloxane; poly-dimethylsiloxanes comprising alkyl, alkoxy or phenyl groups, that are pendant or at the end of a silicone chain, these groups containing from 2 to 24 carbon atoms; phenylsilicones, for instance phenyltrimethicones, phenyldimethicones, phenyltrimethylsiloxydiphenylsiloxanes, diphenyldimethicones, diphenylmethyl-diphenyltrisiloxanes, 2-phenylethyltrimethylsiloxysilicates and polymethylphenylsiloxanes;

mixtures thereof.

In the list of oils mentioned above, the expression "hydrocarbon-based oil" means any oil mainly comprising carbon and hydrogen atoms, and optionally ester, ether, fluoro, carboxylic acid and/or alcohol groups. The other fatty substances that may be present in the oily phase include, for example, fatty acids containing from 8 to 30 carbon atoms, for instance stearic acid, lauric acid, palmitic acid and oleic acid; waxes, for instance lanolin, beeswax, carnauba wax or candelilla wax, paraffin waxes, lignite wax or microcrystalline waxes, ceresin or ozokerite, synthetic waxes such as polyethylene waxes, Fischer-Tropsch waxes; gums such as silicone gums (dimethiconol); silicone resins such as trifluoromethyl-C1-4-alkyldimethicone and trifluoropropyl-dimethicone; and silicone elastomers, for instance the products sold under the name "KSG" by the company Shin-Etsu, under the name "Trefil", "BY29" or "EPSX" by the company Dow Corning, or under the name "Gransil" by the company Grant Industries.

These fatty substances may be chosen in a varied manner by a person skilled in the art so as to prepare a composition having the desired properties, for example in terms of consistency or texture, in view of this disclosure.

When it is present, the amount of oily phase is not limited and may range, for example, from 0.01% to 50% by weight and preferably from 0.1% to 30% by weight relative to the total weight of the composition.

According to one particularly advantageous embodiment of the invention, the composition comprises at least one volatile oil. Specifically, the inventor has demonstrated that this type of oil improves the optical properties of the composition comprising the organosilicon-based open hollow sphere portions described above.

The expression "volatile oils" means oils having, at a temperature of 20° C., a vapour pressure of greater than 1 mbar. The vapour pressure is defined as being the pressure at which a liquid and its vapour are in equilibrium at a given temperature. Useful volatile oils that may be mentioned, inter alia, include cyclic or linear silicones containing from 2 to 6 silicon atoms, such as cyclohexasiloxane, dodecamethylpentasiloxane, decamethyltetrasiloxane, octamethyltrisiloxane and hexamethyldisiloxane. Mention may also be made of branched hydrocarbons, for instance isododecanes, and also volatile perfluoroalkanes such as dodecafluoropentane and tetradecafluorohexane, sold under the names "PF 5050®" and "PF 5060®" by the company 3M, and perfluoromorpholine derivatives, such as 4-trifluoromethyl perfluoromorpholine sold under the name "PF 5052®" by the company 3M.

The composition according to the invention may also contain various adjuvants such as those commonly used in cosmetics, such as emulsifiers; fillers; sequestering agents; colorants; fragrances; and thickeners and gelling agents. The amounts and nature of these various adjuvants is preferably chosen so as not to harm the optical properties of the composition.

The emulsions generally contain at least one emulsifier selected from the group consisting of amphoteric, anionic, cationic and nonionic emulsifiers, used alone or as a mixture, and optionally a co-emulsifier. The emulsifiers are chosen in a suitable manner depending on the emulsion to be obtained (e.g., W/O or O/W). The emulsifier and the co-emulsifier are generally present in the composition in a proportion that may range, for example, from 0.3% to 30% by weight and preferably from 0.5% to 20% by weight relative to the total weight of the composition.

Examples of emulsifiers that may be mentioned for the W/O emulsions include dimethicone copolyols such as the mixture of cyclomethicone and of dimethicone copolyol, sold under the name "DC 5225 C" by the company Dow Corning, and alkyldimethicone copolyols, such as the laurylmethicone copolyol sold under the name "Dow Corning 5200 Formulation Aid" by the company Dow Corning, the cetyldimethicone copolyol sold under the name Abil EM 90® by the company Goldschmidt, or the mixture of cetyldimethicone copolyol, polyglyceryl-4 isostearate and hexyl laurate, sold under the name Abil WE09® by the company Goldschmidt. One or more co-emulsifiers may also be added thereto, which may be advantageously selected from the group consisting of the group comprising alkylated esters of polyol. Alkylated esters of polyol that may especially be mentioned include glycerol and/or sorbitan esters, for example polyglyceryl isostearate, such as the product sold under the name Isolan GI 34 by the company Goldschmidt, sorbitan isostearate, such as the product sold under the name Arlacel 987 by the company ICI, sorbitan glyceryl isostearate, such as the product sold under the name Arlacel 986 by the company ICI, and mixtures thereof.

Surfactants for W/O emulsions that may also be used include a crosslinked elastomeric solid organopolysiloxane comprising at least one oxyalkylene group, such as those obtained according to the procedure of Examples 3, 4 and 8 of document U.S. Pat. No. 5,412,004 and of the examples of document U.S. Pat. No. 5,811,487, especially the product of Example 3 (synthesis example) of U.S. Pat. No. 5,412,004, and such as the product sold under the reference KSG 21 by the company Shin-Etsu.

Examples of emulsifiers that may be mentioned for the O/W emulsions include nonionic surfactants, and especially esters of polyols and of fatty acids with a saturated or unsaturated chain containing, for example, from 8 to 24 carbon atoms and better still from 12 to 22 carbon atoms, and the oxyalkylenated derivatives thereof, i.e. derivatives containing oxyethylenated and/or oxypropylenated units, such as the glyceryl esters of $C_8$-$C_{24}$ fatty acids, and the oxyalkylenated derivatives thereof the polyethylene glycol esters of $C_8$-$C_{24}$ fatty acids, and the oxyalkylenated derivatives thereof; the sorbitol esters of $C_8$-$C_{24}$ fatty acids, and the oxyalkylenated derivatives thereof; the sugar (sucrose, glucose or alkylglucose) esters of $C_8$-$C_{24}$ fatty acids, and the oxyalkylenated derivatives thereof; the ethers of fatty alcohols; the sugar ethers of $C_8$-$C_{24}$ fatty alcohols, and mixtures thereof.

Glyceryl esters of fatty acids that may especially be mentioned include glyceryl stearate (glyceryl mono-, di- and/or tristearate) (CTFA name: glyceryl stearate) or glyceryl ricinoleate and mixtures thereof.

Polyethylene glycol esters of fatty acids that may especially be mentioned include polyethylene glycol stearate (polyethylene glycol mono-, di- and/or tristearate) and more especially polyethylene glycol 50 OE monostearate (CTFA name: PEG-50 stearate), polyethylene glycol 100 OE monostearate (CTFA name: PEG-100 stearate) and mixtures thereof.

It is also possible to use mixtures of these surfactants, for instance the product containing glyceryl stearate and PEG-100 stearate, sold under the name Arlacel 165 by the company Uniqema, and the product containing glyceryl stearate (glyceryl mono-distearate) and potassium stearate, sold under the name Tegin by the company Goldschmidt (CTFA name: glyceryl stearate SE).

Fatty acid esters of glucose or of alkylglucose that may be mentioned in particular include glucose palmitate, alkylglucose sesquistearates, for instance methyl glucose sesquistearate, alkylglucose palmitates, for instance methylglucose palmitate or ethylglucose palmitate, fatty esters of methylglucoside and more especially the diester of methylglucoside and of oleic acid (CTFA name: Methyl glucose dioleate); the mixed ester of methylglucoside and of the oleic acid/hydroxystearic acid mixture (CTFA name: Methyl glucose dioleate/hydroxysterate); the ester of methylglucoside and of isostearic acid (CTFA name: Methyl glucose isostearate); the ester of methylglucoside and of lauric acid (CTFA name: Methyl glucose laurate); the mixture of the monoester and diester of methylglucoside and of isostearic acid (CTFA name: Methyl glucose sesquiisostearate); the mixture of the monoester and diester of methylglucoside and of stearic acid (CTFA name: Methyl glucose sesquistearate) and in particular the product sold under the name Glucate SS by the company Amerchol, and mixtures thereof.

Examples of oxyethylenated ethers of a fatty acid and of glucose or of alkylglucose that may be mentioned include the oxyethylenated ethers of a fatty acid and of methylglucose, and in particular the polyethylene glycol ether of the diester of methyl glucose and of stearic acid containing about 20 mol of ethylene oxide (CTFA name: PEG-20 methyl glucose distearate), such as the product sold under the name Glucam E-20 distearate by the company Amerchol; the polyethylene glycol ether of the mixture of monoester and diester of methylglucose and of stearic acid containing about 20 mol of ethylene oxide (CTFA name: PEG-20 methyl glucose sesquistearate) and in particular the product sold under the name Glucamate SSE-20 by the company Amerchol, and the product sold under the name Grillocose PSE-20 by the company Goldschmidt, and mixtures thereof.

Examples of sucrose esters that may be mentioned include sucrose palmitostearate, sucrose stearate and sucrose monolaurate.

Examples of ethers of fatty alcohols that may be mentioned include polyethylene glycol ethers of fatty alcohols containing from 8 to 30 carbon atoms and especially from 10 to 22 carbon atoms, such as polyethylene glycol ethers of cetyl alcohol, stearyl alcohol or cetearyl alcohol (mixture of cetyl and stearyl alcohol). Examples that may be mentioned include ethers comprising from 1 to 200 and preferably from 2 to 100 oxyethylene groups, such as those of CTFA name Ceteareth-20 and Ceteareth-30, and mixtures thereof.

Sugar ethers that may especially be mentioned include alkylpolyglucosides, for example decylglucoside, for instance the product sold under the name Mydol 10 by the company Kao Chemicals, the product sold under the name Plantaren 2000 by the company Henkel, and the product sold under the name Oramix NS 10 by the company SEPPIC; caprylyl/capryl glucoside, for instance the product sold under the name Oramix CG 110 by the company SEPPIC or under the name Lutensol GD 70 by the company BASF; laurylglucoside, for instance the products sold under the names Plantaren 1200 N and Plantacare 1200 by the company Henkel; cocoglucoside, for instance the product sold under the name Plantacare 818/UP by the company Henkel; cetostearyl glucoside optionally as a mixture with cetostearyl alcohol, sold, for example, under the name Montanov 68 by the company SEPPIC, under the name Tego-Care CG90 by the company Goldschmidt and under the name Emulgade KE3302 by the company Henkel; arachidyl glucoside, for example in the form of the mixture of arachidyl alcohol and behenyl alcohol and arachidyl glucoside, sold under the name Montanov 202 by the company SEPPIC; cocoylethylglucoside, for example in the form of a mixture (35/65) with cetyl and stearyl alcohol, sold under the name Montanov 82 by the company SEPPIC, and mixtures thereof.

As indicated above, depending on the fluidity of the composition that it is desired to obtain, one or more gelling agents, especially hydrophilic gelling agents, i.e. water-soluble or water-dispersible gelling agents, may be incorporated into the composition.

Hydrophilic gelling agents that may be mentioned in particular include water-soluble or water-dispersible thickening polymers. These polymers may be chosen especially from: modified or unmodified carboxyvinyl polymers, such as the products sold under the names Carbopol (CTFA name: carbomer) and Pemulen (CTFA name: Acrylates/C10-30 alkyl acrylate crosspolymer) by the company Goodrich; polyacrylates and polymethacrylates such as the products sold under the names Lubrajel and Norgel by the company Guardian or under the name Hispagel by the company Hispano Chimica; polyacrylamides; optionally crosslinked and/or neutralized 2-acrylamido-2-methylpropane sulfonic acid polymers and copolymers, for instance the poly(2-acrylamido-2-methylpropane-sulfonic acid) sold by the company Clariant under the name "Hostacerin AMPS" (CTFA name: ammonium polyacryldimethyltauramide); crosslinked anionic copolymers of acrylamide and of AMPS, which are in the form of a W/O emulsion, such as those sold under the name Sepigel 305 (CTFA name: Polyacrylamide/C13-14 Isoparaffin/Laureth-7) and under the name Simulgel 600 (CTFA name: Acrylamide/Sodium acryloyldimethyltaurate copolymer/Isohexadecane/Polysorbate 80) by the company SEPPIC; polysaccharide biopolymers, for instance xanthan gum, guar gum, carob gum, acacia gum, scleroglucans, chitin and chitosan derivatives, carrageenans, gellans, alginates, celluloses such as microcrystalline cellulose, carboxymethylcellulose, hydroxymethylcellulose and hydroxypropylcellulose; and mixtures thereof.

Examples of lipophilic gelling agents that may be mentioned include modified clays such as modified magnesium silicate (Bentone Gel VS38 from Rheox), or hectorite modified with distearyldimethylammonium chloride (CTFA name: Disteardimonium hectorite) sold under the name Bentone 38 CE by the company Rheox.

As mentioned previously, the composition according to the invention may also comprise fillers, possibly having a matting effect capable of reinforcing the effects of the sphere portions according to the invention.

Examples of fillers that may be mentioned include polyamide (Nylon) particles and especially the microbeads sold under the name Orgasol by the company Atochem, or nylon fibres; polyethylene powders; microspheres based on acrylic copolymers, such as those made of ethylene glycol dimethacrylate/lauryl methacrylate copolymer sold by the company Dow Corning under the name Polytrap; the polymethyl methacrylate microspheres sold under the name Microsphere M-100 by the company Matsumoto or under the name Covabead LH 85 by the company Wackherr; melamine-formaldehyde or urea-formaldehyde resin particles; poly(tetrafluoroethylene) particles; ethylene-acrylate copolymer powders, for instance those sold under the name Flobeads by the company Sumitomo Seika Chemicals; expanded powders such as hollow microspheres and especially microspheres formed from a terpolymer of vinylidene chloride, acrylonitrile and methacrylate, and sold under the name Expancel by the company Kemanord Plast under the references 551 DE 12 (particle size of about 12 μm and mass of a unit volume of 40 kg/m$^3$), 551 DE 20 (particle size of about 30 μm and mass of a unit volume of 65 kg/m$^3$) and 551 DE 50 (particle size of about 40 μm), or the polyacrylonitrile microspheres sold under the name Micropearl F 80 ED by the company Matsumoto; powders of natural organic materials such as starch powders, especially of crosslinked or non-crosslinked maize, wheat or rice starch, such as the powders of starch crosslinked with octenylsuccinate anhydride, sold under the name Dry-Flo by the company National Starch, or cellulose microbeads; silicone resin microbeads, such as those sold under the name Tospearl by the company Toshiba Silicone, especially Tospearl 240; and mixtures thereof.

Other examples of matting agents that may be used in the composition according to the invention include polymers comprising units with an LCST, as described in patent application FR-2 838 345; copolymers of vinylpyrrolidone and of 1-triacontene; and clays.

To reinforce the effects of the composition according to the invention, it may also, or as a variant, contain one or more active agents that complement the effect obtained using the silicone-based hollow sphere portions.

For an application in particular in caring for or making up greasy skin, the composition according to the invention may comprise at least one active agent selected from the group consisting of: desquamating agents, anti-seborrhoeic agents, antimicrobial agents and calmatives.

For an application in particular in caring for or making up aged skin, the composition according to the invention may comprise at least one active agent selected from the group consisting of: desquamating agents or moisturizers; depigmenting or anti-pigmenting agents; anti-glycation agents; anti-NO agents; agents for stimulating the synthesis of dermal or epidermal macromolecules and/or for preventing their degradation; agents for stimulating fibroblast or keratinocyte proliferation and/or keratinocyte differentiation; muscle relaxants or dermo-decontracting agents; free-radical scavengers or anti-pollution agents; tensioning agents; and agents acting on the capillary circulation.

Non-limiting examples of such active agents will now be given.
1. Desquamating Agents and Moisturizers The term "desquamating agent" means any compound capable of acting:
either directly on desquamation by promoting exfoliation, such as β-hydroxy acids, in particular salicylic acid and its derivatives (including 5-n-octanoylsalicylic acid); α-hydroxy acids, such as glycolic acid, citric acid, lactic acid, tartaric acid, malic acid or mandelic acid; urea; gentisic acid; oligofucoses; cinnamic acid; extract of *Saphora japonica*; resveratrol and certain jasmonic acid derivatives;
or on the enzymes involved in the desquamation or degradation of corneodesmosomes, glycosidases, stratum corneum chymotryptic enzyme (SCCE), or even other proteases (trypsin, chymotrypsin-like). Mention may be made of agents for chelating mineral salts: EDTA; N-acyl-N,N',N'-ethylenediaminetriacetic acid; aminosulfonic compounds and in particular (N-2-hydroxyethylpiperazine-N-2-ethane)sulfonic acid (HEPES); 2-oxothiazolidine-4-carboxylic acid (procysteine) derivatives; α-amino acid derivatives of the type such as glycine (as described in EP-0 852 949 and sodium methylglycinediacetate sold by BASF under the trade name Trilon M); honey; sugar derivatives such as O-octanoyl-6-D-maltose and N-acetylglucosamine.

The term "moisturizer" means:
either a compound acting on the barrier function, in order to keep the stratum corneum moisturized, or an occlusive compound. Mention may be made of ceramides, sphingoid-based compounds, lecithins, glycosphingolipids, phospholipids, cholesterol and its derivatives, phytosterols (stigmasterol, β-sitosterol or campesterol), essential fatty acids, 1,2-diacylglycerol, 4-chromanone, pentacyclic triterpenes such as ursolic acid, petroleum jelly and lanolin;
or a compound that directly increases the water content of the stratum corneum, such as threalose and its derivatives, hyaluronic acid and its derivatives, glycerol, pentanediol, sodium pidolate, serine, xylitol, sodium lactate, polyglyceryl acrylate, ectoin and its derivatives, chitosan, oligosaccharides and polysaccharides, cyclic carbonates, N-lauroylpyrrolidonecarboxylic acid and N-α-benzoyl-L-arginine;

or a compound that activates the sebaceous glands, such as steroid derivatives (including DHEA the 7-oxido and/or 17-alkyl derivatives thereof, and sapogenins), methyl dihydrojasmonate and vitamin D and its derivatives.

2. Depigmenting, Anti-Pigmenting or Pro-Pigmenting Agent

The depigmenting or anti-pigmenting agents that may be incorporated into the composition according to the present invention comprise, for example, the following compounds: kojic acid; ellagic acid; arbutin and its derivatives such as those described in patent applications EP-895 779 and EP-524 109; hydroquinone; aminophenol derivatives such as those described in patent applications WO 99/10318 and WO 99/32077, and in particular N-cholesteryloxycarbonyl-para-aminophenol and N-ethyloxycarbonyl-para-aminophenol; iminophenol derivatives, in particular those described in patent application WO 99/22707; L-2-oxothiazolidine-4-carboxylic acid or procysteine, and also its salts and esters; calcium D-pantheteine sulfonate; ascorbic acid and its derivatives, especially ascorbyl glucoside; and plant extracts, in particular extracts of liquorice, of mulberry, of skullcap and of *Bacopa monnieri*, without this list being limiting.

Pro-pigmenting agents that may be mentioned include the extract of burnet (*Sanguisorba officinalis*) sold by the company Maruzen, and extracts of chrysanthemum (*Chrysanthemum morifolium*).

3. Anti-Glycation Agent

The term "anti-glycation agent" means a compound for preventing and/or reducing the glycation of skin proteins, in particular of dermal proteins such as collagen.

Examples of anti-glycation agents are plant extracts of the Ericacea family, such as an extract of blueberry (*Vaccinium angustifolium*); ergothioneine and its derivatives; and hydroxystilbenes and their derivatives, such as resveratrol and 3,3',5,5'-tetrahydroxystilbene. These anti-glycation agents are described in patent applications FR 2 802 425, FR 2 810 548, FR 2 796 278 and FR 2 802 420, respectively. Resveratrol is particularly preferred for use in this invention.

4. NO-Synthase Inhibitor

Examples of NO-synthase inhibitors that are suitable for use in the present invention especially comprise a plant extract of the species *Vitis vinifera* which is sold especially by the company Euromed under the name "Leucocyanidines de raisins extra", or by the company Indena under the name Leucoselect®, or finally by the company Hansen under the name "Extrait de marc de raisin"; a plant extract of the species *Olea europaea* which is preferably obtained from olive tree leaves and is sold especially by the company Vinyals in the form of a dry extract, or by the company Biologia & Technologia under the trade name Eurol BT; and a plant extract of the species *Gingko biloba* which is preferably a dry aqueous extract of this plant sold by the company Beaufour under the trade name "*Gingko biloba* extrait standard".

5. Anti-Seborrhoeic Agent

When the composition according to the invention comprises an anti-seborrhoeic agent such as a 5α-reductase inhibitor, this agent may be chosen especially from:

retinoids, and in particular retinol;

sulfur and sulfur derivatives;

zinc salts such as zinc lactate, gluconate, pidolate, carboxylate, salicylate and/or cysteate;

selenium chloride;

vitamin B6 or pyridoxine;

mixture of caprylolyl glycine, sarcosine and extract of *Cinnamomum zeylanicum* sold especially by the company SEPPIC under the trade name Sepicontrol A5®;

an extract of *Laminaria saccharina* sold especially by the company SECMA under the trade name Phiorogine®;

an extract of *Spiraea ulmaria* sold especially by the company Silab under the trade name Sebonormine®;

plant extracts from the species *Arnica montana, Cinchona succirubra, Eugenia caryophyllata, Humulus lupulus, Hypericum perforatum, Mentha piperita, Rosmarinus officinalis, Salvia oficinalis* and *Thymus vulgaris*, all sold, for example, by the company Maruzen;

an extract of *Serenoa repens* sold especially by the company Euromed;

plant extracts of the genus *Silybum*;

plant extracts containing sapogenins and in particular extracts of diosgenin-rich or hecogenin-rich Dioscorea plants; and extracts of *Eugenia caryophyllata* containing eugenol or eugenyl glucoside.

6. Agent for Stimulating the Synthesis of Dermal or Epidermal Macromolecules and/or for Preventing their Degradation Among the active agents for stimulating dermal macromolecules or for preventing their degradation, mention may be made of those that act:

either on collagen synthesis, such as extracts of *Centella asiatica*; asiaticosides and derivatives; ascorbic acid or vitamin C and its derivatives; synthetic peptides such as iamin, biopeptide CL or the palmitoyloligopeptide sold by the company Sederma; peptides extracted from plants, such as the soybean hydrolysate sold by the company Coletica under the trade name Phytokine®; and plant hormones such as auxins;

or on elastin synthesis, such as the extract of *Saccharomyces cerivisiae* sold by the company LSN under the trade name Cytovitin®; and the extract of the alga *Macrocystis pyrifera* sold by the company SECMA under the trade name Kelpadelie®;

or on glycosaminoglycan synthesis, such as the product of fermentation of milk with *Lactobacillus vulgaris*, sold by the company Brooks under the trade name Biomin Yogourth®; the extract of the brown alga *Padina pavonica* sold by the company Alban Müller under the trade name HSP3®; and the extract of *Saccharomyces cerevisiae* available especially from the company Silab under the trade name Firmalift® or from the company LSN under the trade name Cytovitin®;

or on fibronectin synthesis, such as the extract of the zooplankton Salina sold by the company Seporga under the trade name GP4G®;

the yeast extract available especially from the company Alban Müller under the trade name Drieline®; and the palmitoyl pentapeptide sold by the company Sederma under the trade name Matrixil®;

or on the inhibition of metalloproteases (MMP), such as, more particularly, MMP 1, 2, 3 or 9. Mention may be made of: retinoids and derivatives, oligopeptides and lipopeptides, lipoamino acids, the malt extract sold by the company Coletica under the trade name Collalift®; extracts of blueberry or of rosemary; lycopene; isoflavones, their derivatives or plant extracts containing them, in particular extracts of soybean (sold, for example, by the company Ichimaru Pharcos under the trade name Flavosterone SB®), of red clover, of flax, of kakkon, or of sage;

or on the inhibition of serine proteases such as leukocyte elastase or cathepsin G. Mention may be made of: the peptide extract of *Leguminosa* seeds (*Pisum sativum*) sold by the company LSN under the trade name Parelastyl®; and heparinoids and pseudodipeptides such as {2-[acetyl(3-trifluoromethylphenyl)amino]-3-methylbutyrylamino}acetic acid.

Among the active agents that stimulate epidermal macromolecules, such as fillagrin and keratins, mention may be made especially of the extract of lupin sold by the company Silab under the trade name Structurine®; the extract of beech *Fagus sylvatica* buds sold by the company Gattefosse under the trade name Gatuline®; and the extract of the zooplankton Salina sold by the company Seporga under the trade name GP4G®.

7. Agent for Stimulating Fibroblast or Keratinocyte Proliferation and/or Keratinocyte Differentiation The agents for stimulating fibroblast proliferation that may be used in the composition according to the invention may be chosen, for example, from plant proteins or polypeptides, extracted especially from soybean (for example an extract of soybean sold by the company LSN under the name Eleseryl SH-VEG 8® or sold by the company Silab under the trade name Raffermine®); and plant hormones such as giberrellins and cytokinins.

The agents for stimulating keratinocyte proliferation that may be used in the composition according to the invention especially comprise retinoids such as retinol and its esters, including retinyl palmitate; phloroglucinol; extracts of walnut cakes sold by the company Gattefosse; and extracts of *Solanum tuberosum* sold by the company Sederma.

The agents for stimulating keratinocyte differentiation comprise, for example, minerals such as calcium; the extract of lupin sold by the company Silab under the trade name Photopreventine®; sodium β-sitosteryl sulfate sold by the company Seporga under the trade name Phytocohesine®; and the extract of corn sold by the company Solabia under the trade name Phytovityl®; and lignans such as secoisolariciresinol.

8. Muscle Relaxant or Dermo-Decontracting Agent

Among the muscle relaxants or dermo-decontracting agents that may be used in the composition according to the invention the following deserve particular mention: alverine and its salts, manganese gluconate, Diazepam, Argireline hexapeptide R sold by the company Lipotec, certain secondary and tertiary carbonyl amines, adenosine, sapogenins and natural extracts, in particular of wild yam, containing them, and also extracts of *Boswellia serrata*.

9. Antimicrobial Agent

The antimicrobial agents that may be used in the composition according to the invention may be chosen especially from 2,4,4'-trichloro-2'-hydroxydiphenyl ether (or triclosan), 3,4,4'-trichlorobanilide, phenoxyethanol, phenoxypropanol, phenoxyisopropanol, hexamidine isethionate, metronidazole and its salts, micronazole and its salts, itraconazole, terconazole, econazole, ketoconazole, saperconazole, fluconazole, clotrimazole, butoconazole, oxiconazole, sulfaconazole, sulconazole, terbinafine, ciclopirox, ciclopiroxolamine, undecylenic acid and its salts, benzoyl peroxide, 3-hydroxybenzoic acid, 4-hydroxybenzoic acid, phytic acid, N-acetyl-L-cysteine acid, lipoic acid, azelaic acid and its salts, arachidonic acid, resorcinol, 2,4,4'-trichloro-2'-hydroxydiphenyl ether, 3,4,4'-trichlorocarbanalide, octopirox, octoxyglycerine, octanoylglycine, caprylyl glycol, 10-hydroxy-2-decanoic acid, dichlorophenylimidazole dioxolane and its derivatives described in patent WO 93/18743, farnesol and phytosphingosines, and mixtures thereof.

The preferred antimicrobial agents are triclosan, phenoxyethanol, octoxyglycerine, octanoylglycine, 10-hydroxy-2-decanoic acid, caprylyl glycol, farnesol and azelaic acid.

10. Tensioning Agent

The term "tensioning agent" means a compound capable of exerting tension on the skin, the effect of which is to temporarily fade out irregularities on the skin's surface, such as wrinkles and fine lines.

Among the tensioning agents that may be used in the composition according to the present invention, mention may be made especially of:

(1) synthetic polymers such as polyurethane latices or acrylic-silicone latices, in particular those described in patent application EP-1 038 519, such as a propylthio(polymethyl acrylate), propylthio(polymethyl methacrylate) and propylthio(polymethacrylic acid) grafted polydimethylsiloxane, or alternatively a propylthio(polyisobutyl methacrylate) and propylthio(polymethacrylic acid) grafted polydimethylsiloxane. Such grafted silicone polymers are sold especially by the company 3M under the trade names VS 80, VS 70 or LO21.

(2) polymers of natural origin, especially (a) polyholosides, for example (i) in the form of starch derived especially from rice, corn, potato, cassava, pea, *Triticum aestivum* wheat, oat, etc. or (ii) in the form of carrageenans, alginates, agars, gelans, cellulose-based polymers and pectins, advantageously as an aqueous dispersion of gel microparticles, and (b) latices consisting of shellac resin, sandarac gum, dammar resins, elemi gums, copal resins and cellulose-based derivatives, and mixtures thereof, (3) plant proteins and protein hydrolysates, in particular from corn, rye, *Triticum aestivum* wheat, buckwheat, sesame, spelt, pea, bean, lentil, soybean and lupin, (3) mixed silicates, especially phyllosilicates and in particular Laponites, (4) wax microparticles chosen, for example, from carnauba wax, candelilla wax and alfalfa wax, (5) colloidal particles of mineral filler with a number-average diameter of between 0.1 and 100 nm and preferably between 3 and 30 nm, chosen, for example, from: silica, silica-alumina composites, cerium oxide, zirconium oxide, alumina, calcium carbonate, barium sulfate, calcium sulfate, zinc oxide and titanium dioxide.

11. Anti-Pollution Agent or Free-Radical Scavenger

The term "anti-pollution agent" means any compound capable of trapping ozone, monocyclic or polycyclic aromatic compounds such as benzopyrene and/or heavy metals such as cobalt, mercury, cadmium and/or nickel. The term "free-radical scavenger" means any compound capable of trapping free radicals.

As ozone-trapping agents that may be used in the composition according to the invention, mention may be made in particular of vitamin C and its derivatives including ascorbyl glucoside; phenols and polyphenols, in particular tannins, ellagic acid and tannic acid; epigallocatechin and natural extracts containing it; extracts of olive tree leaf; extracts of tea, in particular of green tea; anthocyans; extracts of rosemary; phenol acids, in particular chorogenic acid; stilbenes, in particular resveratrol; sulfur-containing amino acid derivatives, in particular S-carboxymethylcysteine; ergothioneine; N-acetylcysteine; chelating agents, for instance N,N'-bis(3,4,5-trimethoxybenzyl)ethylenediamine or one of its salts, metal complexes or esters; carotenoids such as crocetin; and various starting materials, for instance the mixture of arginine, histidine ribonucleate, mannitol, adenosine triphosphate, pyridoxine, phenylalanine, tyrosine and hydrolysed RNA, sold by Laboratoires Serobiologiques under the trade name CPP LS 2633-12F®, the water-soluble fraction of corn sold by the company Solabia under the trade name Phytovityl®, the mixture of extract of fumitory and of extract of lemon sold under the name Unicotrozon C-49® by the company Induchem, and the mixture of extracts of ginseng, of apple, of peach, of wheat and of barley, sold by the company Provital under the trade name Pronalen Bioprotect®.

As agents for trapping monocyclic or polycyclic aromatic compounds, which may be used in the composition according to the invention, mention may be made in particular of tannins such as ellagic acid; indole derivatives, in particular 3-indolecarbinol; extracts of tea, in particular of green tea, extracts of water hyacinth or *Eichhornia crassipes*; and the water-soluble fraction of corn sold by the company Solabia under the trade name Phytovityl®.

Finally, as heavy-metal-trapping agents that may be used in the composition according to the invention, mention may be made in particular of chelating agents such as EDTA, the pentasodium salt of ethylenediaminetetramethylenephosphonic acid, and N,N'-bis(3,4,5-trimethoxybenzyl)ethylenediamine or one of the salts, metal complexes or esters thereof; phytic acid; chitosan derivatives; extracts of tea, in particular of green tea; tannins such as ellagic acid; sulfur-containing amino acids such as cysteine; extracts of water hyacinth (*Eichhornia crassipes*); and the water-soluble fraction of corn sold by the company Solabia under the trade name Phytovityl®.

The free-radical scavengers that may be used in the composition according to the invention comprise, besides certain anti-pollution agents mentioned above, vitamin E and its derivatives such as tocopheryl acetate; bioflavonoids; coenzyme Q10 or ubiquinone; certain enzymes, for instance catalase, superoxide dismutase, lactoperoxidase, glutathione peroxidase and quinone reductases; glutathione; benzylidenecamphor; benzylcyclanones; substituted naphthalenones; pidolates; phytanetriol; gamma-oryzanol; lignans; and melatonin.

12. Calmatives

As calmatives that may be used in the composition according to the invention, mention may be made of: pentacyclic triterpenes and extracts of plants (e.g.: *Glycyrrhiza glabra*) containing them, for instance β-glycyrrhetinic acid and salts and/or derivatives thereof (glycyrrhetinic acid monoglucoronide, stearyl glycyrrhetinate or 3-stearoyloxyglycyrrhetic acid), ursolic acid and its salts, oleanolic acid and its salts, betulinic acid and its salts, an extract of *Paeonia suffruticosa* and/or *lactiflora*, salicylic acid salts and in particular zinc salicylate, the phycosaccharides from the company Codif, an extract of *Laminaria saccharina*, canola oil, bisabolol and camomile extracts, allantoin, Sepivital EPC (phosphoric diester of vitamins E and C) from SEPPIC, omega-3 unsaturated oils such as musk rose oil, blackcurrant oil, ecchium oil, fish oil, plankton extracts, capryloylglycine, Seppicalm VG (sodium palmitoylproline and *Nymphea alba*) from SEPPIC, an extract of *Pygeum*, an extract of *Boswellia serrata*, an extract of *Centipeda cunnighami*, an extract of *Helianthus annuus*, an extract of *Linum usitatissimum*, tocotrienols, extracts of *Cola nitida*, piperonal, an extract of clove, an extract of *Epilobium angustifolium*, *Aloe vera*, an extract of *Bacopa moniera*, phytosterols, cortisone, hydrocortisone, indomethacin and betamethasone.

13. Agents Acting on the Capillary Circulation

The active agents acting on the capillary circulation (vasoprotective or vasodilating agents) may be selected from the group consisting of flavonoids, ruscogenins, esculosides, escin extracted from common horse chestnut, nicotinates, heperidine methyl chalcone, essential oils of lavender or of rosemary, and extracts of *Ammi visnaga*.

The invention will now be illustrated by the non-limiting examples that follow. In these examples, the amounts are indicated as percentages by weight.

EXAMPLES

Example 1

Cosmetic Compositions

| O/W emulsions | A (comparative) | B | C | D |
|---|---|---|---|---|
| Xanthan gum | 0.20% | 0.20% | 0.20% | 0.20% |
| Crosslinked poly(2-acrylamido-2-methyl-propanesulfonic acid) | 0.40% | 0.40% | 0.40% | 0.40% |
| Cyclohexasiloxane | 10.0% | 10.0% | 10.0% | 10.0% |
| Sodium hydroxide | 0.01% | 0.01% | 0.01% | 0.01% |
| Glycerol | 5.00% | 5.00% | 5.00% | 5.00% |
| Stearyl alcohol | 1.00% | 1.00% | 1.00% | 1.00% |
| Polyoxyethylene glyceryl stearate (100 OE) | 2.00% | 2.00% | 2.00% | 2.00% |
| Dimyristyl tartrate, cetearyl alcohol, oxyethylenated (7 OE) $C_{12-15}$ fatty alcohols and oxyethylenated (25 OE) and oxypropylenated (25 OE) lauryl alcohol | 1.50% | 1.50% | 1.50% | 1.50% |
| Spherical particles of crosslinked organopolysiloxane [1] | 5.00% | | | |
| Hemispherical particles of crosslinked organopolysiloxane [2] | | 5.00% | | |
| Hemispherical particles of crosslinked organopolysiloxane [3] | | | 5.00% | |
| Hemispherical particles of crosslinked organopolysiloxane [4] | | | | 5.00% |
| Preserving agents | 0.70% | 0.70% | 0.70% | 0.70% |
| Water | qs 100% | qs 100% | qs 100% | qs 100% |

[1] Spherical particles of diameter 3.2 μm consisting of a dimethiconol/silsesquioxane copolymer
[2] Particles consisting of the crosslinked organosilicone TAK-110 (methylsilanol/silicate crosslinked polymer) from the company Takemoto Oil & Fat, in the form of a bowl 2.5 μm wide, 1.5 μm high and 350 nm thick
[3] Particles consisting of the crosslinked organosilicone TAK-110 (methylsilanol/silicate crosslinked polymer) from the company Takemoto Oil & Fat, in the form of a bowl 2.5 μm wide, 1.5 μm high and 600 nm thick
[4] Particles consisting of the crosslinked organosilicone TAK-110 (methylsilanol/silicate crosslinked polymer) from the company Takemoto Oil & Fat.

These compositions are prepared in a manner that is conventional for a person skilled in the art, by adding, with stirring, the oily phase heated to 65° C. to the hot aqueous phase.

Example 2

In Vitro Evaluation of the Optical Properties

The matt effect obtained with compositions B to D according to the invention, and with composition A given as a comparative example, was measured using a contrast card (Prufkarte type 24/5-250 cm²) sold by the company Erichsen. The composition was spread at a rate of 2 mg/cm² using a mechanical film spreader. The composition was then dried overnight at a temperature of 37° C., and the reflection was then measured using a gonioreflectometer. The result obtained is the ratio R between the specular reflection and the diffuse reflection. The value of R is proportionately smaller the greater the matting effect.

| Composition | A | B | C | D |
|---|---|---|---|---|
| R | 2.00 ± 0.09 | 0.85 ± 0.10 | 0.88 ± 0.02 | 0.55 ± 0.05 |

These in vitro results show that with a 5% (active material) concentration of hemispherical particles of organopolysiloxane, the matt result obtained is very much superior to that obtained with the comparative formulation containing organosilicon-based spherical particles.

Example 3

In Vivo Evaluation

The matting effect and the cosmetic aspects of a formulation corresponding to composition B of Example 1, but containing 8% of hemispherical particles of organopolysiloxane instead of 5%, were evaluated by a panel of seven women with greasy skin. It was judged that this composition made the skin matt and gave it a fine grain, the pores appearing less dilated and the complexion more unified. A soft-focus effect on the defects was observed.

Example 4

In Vivo Evaluation

The optical effects on the skin of a composition corresponding to composition B of Example 1, but containing 8% by weight of hemispherical particles of crosslinked organopolysiloxane obtained under the trade name NLK-506 from Takemoto Oil and Fat, were evaluated on a panel of six women with greasy skin and having irregularities of the microrelief.

It was observed that the test composition instantaneously matted the highlights on the surface of the skin and reduced the visibility of the microrelief by making the grain of the skin fine, the pores appearing less dilated.

The above written description of the invention provides a manner and process of making and using it such that any person skilled in this art is enabled to make and use the same, this enablement being provided in particular for the subject matter of the appended claims, which make up a part of the original description and including a composition in the form of an emulsion comprising, in a physiologically acceptable medium, portions of hollow spheres consisting of organosilicon-based material, the spheres having a mean diameter ranging from 0.05 to 10 μm. Another embodiment of the invention fully described and enabled include a cosmetic process for fading out skin surface defects using the invention compositions. In preferred embodiments the amount of invention hollow sphere portions present in the invention compositions, and/or the amount applied in the invention processes, is an amount sufficient to effectively treat, prevent, or treat or prevent the appearance of, skin surface defects, aged skin, greasy or combination skin, skin sheen, pore appearance, shadows under the eyes, marks, wrinkles and/or fine lines.

As used above, the phrases "selected from the group consisting of," "chosen from," and the like include mixtures of the specified materials.

All references, patents, applications, tests, standards, documents, publications, brochures, texts, articles, etc. mentioned herein are incorporated herein by reference. Where a numerical limit or range is stated, the endpoints are included. Also, all values and subranges within a numerical limit or range are specifically included as if explicitly written out.

The above description is presented to enable a person skilled in the art to make and use the invention, and is provided in the context of a particular application and its requirements. Various modifications to the preferred embodiments will be readily apparent to those skilled in the art, and the generic principles defined herein may be applied to other embodiments and applications without departing from the spirit and scope of the invention. Thus, this invention is not intended to be limited to the embodiments shown, but is to be accorded the widest scope consistent with the principles and features disclosed herein.

The invention claimed is:

1. A composition in the form of an emulsion comprising, in a physiologically acceptable medium, portions of hollow spheres consisting of organosilicon-based material, the spheres having a mean diameter ranging from 0.05 to 10 μm, wherein the portions of hollow spheres have a shape formed, in longitudinal cross section, from a small inner arc, a large outer arc and segments linking ends of the respective arcs, a first width (W1) between the ends of the small inner arc ranging from 0.01 to 8 μm on average, a second width (W2) between the ends of the large outer arc ranging from 0.05 to 10 μm on average, and a height of the large outer arc ranging from 0.015 to 8 μm on average, wherein the portions of hollow spheres are substantially hemispherical and comprise a crosslinked polysiloxane of three-dimensional structure consisting of units of formula (I): $SiO_2$ and of formula (II): $R_1SiO_{1.5}$ in which $R^1$ is an organic group containing a carbon atom directly linked to the silicon atom.

2. The composition according to claim 1, wherein the portions of hollow spheres are obtained according to a process comprising: (a) introducing into an aqueous medium, in the presence of a hydrolysis catalyst, and optionally of a surfactant, a compound (I) of formula $SiX_4$ and a compound (II) of formula $RSiY_3$, in which X and Y independently are a $C_1$-$C_4$ alkoxy group, an alkoxyethoxy group containing a $C_1$-$C_4$ alkoxy group, a $C_2$-$C_4$ acyloxy group, an N,N-dialkylamino group containing a $C_1$-$C_4$ alkyl group, a hydroxyl group, a halogen atom or a hydrogen atom, and R is an organic group comprising a carbon atom directly linked to the silicon atom; and (b) placing a mixture resulting from step (a) in contact with an aqueous solution containing at least one polymerization catalyst and optionally at least one surfactant, at a temperature of between 30 and 85° C., for at least two hours.

3. The composition according to claim 2, wherein the compound of formula (I) is selected from the group consisting of: tetramethoxysilane, tetraethoxysilane, tetrabutoxysilane, trimethoxyethoxysilane, tributoxyethoxysilane, tetraacetoxysilane, tetraprop oxysilane, tetraacetoxysilane, tetra(dimethylamino)silane, tetra(diethylamino)silane, silane tetraol, chlorosilane triol, dichlorodisilanol, tetrachlorosilane, chlorotrihydrogenosilane and mixtures thereof.

4. The composition according to claim 2, wherein the compound of formula (II) comprises the organic group R which is unreactive and is selected from the group consisting of: methyltrimethoxysilane, ethyltriethoxysilane, propyltributoxysilane, butyltributoxysilane, phenyltrimethoxyethoxysilane, methyltributoxyethoxysilane, methyltriacetoxysilane, methyltripropoxysilane, methyltriacetoxysilane, methyltri(dimethylamino)silane, methyltri(diethylamino)silane, methylsilane triol, methylchlorodisilanol, methyltrichlorosilane, methyltrihydrogenosilane and mixtures thereof.

5. The composition according to claim 2, wherein the compound of formula (II) comprises the organic group R which is unreactive and is selected from the group consisting of: silanes containing an epoxy group; silanes containing a (meth)acryloxy group; silanes containing an alkenyl group; silanes containing a mercapto group; silanes containing an aminoalkyl group; silanes containing a haloalkyl group; silanes containing a glyceroxy group; silanes containing a ureido group; silanes containing a cyano group, and mixtures thereof.

6. The composition according to claim 2, wherein the X and/or Y is a $C_1$-$C_4$ alkoxy group.

7. The composition according to claim 2, wherein the compound (I) is tetraethoxysilane.

8. The composition according to claim 2, wherein the compound (II) is methyltrimethoxysilane.

9. The composition according to claim 2, wherein, in (a), a molar ratio of the compound (I) to the compound (II) ranges from 30:70 to 50:50.

10. The composition according to claim 9, wherein the molar ratio of the compound (I) to the compound (II) ranges from 35:65 to 45:55.

11. The composition according to claim 9, wherein the molar ratio of the compound (I) to the compound (II) is 40:60.

12. The composition according to claim 2, wherein a weight ratio of water in said aqueous medium to a total amount of the compounds (I) and (II) ranges from 10:90 to 70:30 in (a).

13. The composition according to claim 2, wherein the hydrolysis catalyst and the polymerization catalyst are independently selected from the group consisting of sodium hydroxide, sodium carbonate, acetic acid, sodium dodecylbenzenesulfonate, hydrochloric acid and mixtures thereof.

14. The composition according to claim 2, wherein the surfactant is sodium dodecylbenzenesulfonate.

15. The composition according to claim 1, wherein $R^1$ is an organic group which is unreactive selected from the group consisting of: a methyl, ethyl, propyl, butyl group or a phenyl group.

16. The composition according to claim 1, wherein $R^1$ is a reactive organic group selected from the group consisting of: an epoxy group, a (meth)acryloxy group, an alkenyl group, a mercaptoalkyl, aminoalkyl or haloalkyl group, a glyceroxy group, a ureido group or a cyano group, containing from 2 to 6 carbon atoms.

17. The composition according to claim 15, wherein $R^1$ is a methyl group.

18. The composition according to claim 1, wherein (W2−W1)/2 ranges from 0.05 to 1 μm.

19. The composition according to claim 1, wherein a ratio W2 to (W2−W1)/2 is at least 3.

20. The composition according to claim 19, wherein the ratio W2 to (W2−W1)/2 is greater than 5.

21. The composition according to claim 20, wherein the ratio W2 to (W2−W1)/2 is greater than 10.

22. The composition according to claim 21, wherein the ratio W2 to (W2−W1)/2 is greater than 20.

23. The composition according to claim 1, wherein an amount of portions of hollow spheres is from 0.5% to 10% of the total weight of the composition.

24. The composition according to claim 1, wherein said composition is in the form of an O/W emulsion.

25. The composition according to claim 1, further comprising at least one volatile oil.

26. The composition according to claim 25, wherein the volatile oil is selected from the group consisting of: cyclic or linear silicones containing from 2 to 6 silicon atoms, branched hydrocarbons, volatile perfluoroalkanes, perfluoromorpholine derivatives, and mixtures thereof.

27. The composition according to claim 1, wherein the composition comprises at least one surfactant.

28. The composition according to claim 1, wherein said composition is in the form of an emulsion having an aqueous outer phase.

29. A process for fading out skin surface defects, comprising topically applying to skin in need thereof the composition according to claim 1.

30. The process according to claim 29, wherein said process is a process to reduce sheen of skin and/or to fade out an pores, and wherein the amount of the composition applied is an amount effective to reduce the sheen of the skin and/or to fade out the pores.

31. The process according to claim 29, wherein said process is a process to treat greasy or combination skin.

32. The process according to claim 30, wherein the composition further comprises at least one active agent selected from the group consisting of: desquamating agents, anti-seborrhoeic agents, antimicrobial agents, calmatives and mixtures thereof.

33. The process according to claim 29, wherein said process is a process to fade out shadows under the eyes, marks, wrinkles and/or fine lines.

34. The process according to claim 29, wherein the skin is aged skin.

35. The process according to claim 34, wherein the composition further comprises at least one active agent selected from the group consisting of: desquamating agents or moisturizers; depigmenting or anti-pigmenting agents; anti-glycation agents; anti-NO agents; agents for stimulating the synthesis of dermal or epidermal macromolecules and/or for preventing their degradation; agents for stimulating fibroblast or keratinocyte proliferation and/or keratinocyte differentiation; muscle relaxants or dermo-decontracting agents; free-radical scavengers or anti-pollution agents; tensioning agents; and agents acting on the capillary circulation.

* * * * *